United States Patent [19]
Kung et al.

[11] Patent Number: 4,560,534
[45] Date of Patent: Dec. 24, 1985

[54] POLYMER CATALYST TRANSDUCERS

[75] Inventors: Wei-jen Kung, East Lansing, Mich.; Paul O. Vogelhut, Mishawaka, Ind.

[73] Assignee: Miles Laboratories, Inc., Elkhart, Ind.

[21] Appl. No.: 548,152

[22] Filed: Nov. 2, 1983

[51] Int. Cl.[4] .......... G01N 27/00
[52] U.S. Cl. .......... 422/68; 422/98; 436/151
[58] Field of Search .......... 338/34; 324/71.1; 422/68, 98, 88, 90; 436/155, 151

[56] References Cited

U.S. PATENT DOCUMENTS

| | | | |
|---|---|---|---|
| 3,008,879 | 11/1961 | Harvill | 422/57 |
| 3,421,982 | 1/1969 | Schultz et al. | 435/12 |
| 3,574,072 | 4/1971 | Louvar | 204/72 |
| 3,635,681 | 1/1972 | Rogers | 204/195 X |
| 4,334,880 | 6/1982 | Malmros | 422/68 X |
| 4,413,151 | 11/1983 | Michaelson et al. | 502/159 X |

OTHER PUBLICATIONS

Khan et al.; Homogeneous Catalyst by Metal Complexes; Academic Press, New York 1974, pp. 138–149.
Savvin et al.; Investigation of the Elementary Stages in the Catalytic Decomposition of Hydrogen Peroxide on Metal Oxides by Conductometric Analysis and IR Spectroscopy; Kinet. Catal. 19 (3) (1977) pp. 634–636.
Anderson et al.; Electrode Surface Conductance Measurements in an Electrochemical Cell; J. of Elec. Soc. 121 (12) 1974 pp. 1570–1575.
Pochan et al.; Kinetics of Doping and Degradation of Polyacetylene by Oxygen; Macromolecules 1981, 14, 110–114.
Diaz; Electrochemical Preparation and Characterization of Conducting Polymers; Chemica Scripta 17:145–148 1981.
Pron et al.; Synthesis and Characterization of New Organic Metals Formed by Interaction of $FeCl_3$ with Polyacetylene and Poly(para)phenylene; Mat. Res. Bull. vol. 16 1229–1235 1981.
Frank et al.; Polypyrrole-Coated Semiconductor Electrodes; J. Electrochemical Soc. 82 (1) 992 (1982).
Bull et al.; Incorporation of Catalysts into Electronically Conductive Polymers; J. Electrochemical Soc. vol. 130 No. 7 pp. 1636–1638 1983.
Harvey; Conductance of Germanium in Contact with Aqueous Electrolytes; Annals of the New York Acad. of Sciences, vol. 101; Article 3, pp. 904–914 1963.
Weber et al.; Complexes Derived from Strong Field Ligands, XIX, Magnetic Properties of Transition Metal Derivatives of 4,4′,4″,4‴-Tetrasulfophthalocyanine; Inorganic Chem. vol. 4 No. 4, pp. 469–471 1965.
Fleischer et al.; Thermodynamic and Kinetic Properties of an Iron–Porphyrin System; J. of the Amer. Chem. Soc. 93:13 1971 pp. 3162–3167.
Diaz et al.; Extended Linear Chain Compounds; vol. 3; Plenum Press, New York pp. 417–441 1983.
Chin et al.; Conductivity Method for Determination of Urea; Anal. Chem. 33:12 pp. 1757–1760 1961.
Fisher Scientific Catalog (81), 1981 p. 229.
Bull et al.; Chem. Abstracts 99: 71762e.

*Primary Examiner*—Barry S. Richman
*Assistant Examiner*—Michael S. Gzybowski
*Attorney, Agent, or Firm*—Roger N. Coe

[57] ABSTRACT

Polymer-catalyst transducers are used for detecting one or more constituents in a sample. Changes in conductivity of the polymer-catalyst transducers as a result of electron density changes are measured to provide an indication of a particular constituent present in the sample. Such conductivity changes can be measured using a conductivity meter. The polymer-catalyst transducers are particularly useful for the determination of glucose in whole blood.

10 Claims, 4 Drawing Figures

POLYMER CATALYST TRANSDUCERS

FIELD OF THE INVENTION

The present invention relates generally to the field of analyte detection and, more particularly, to polymer-catalyst transducers and their use for detecting a constituent in a sample.

BACKGROUND OF THE INVENTION

Methods for the analysis of fluid material, e.g., industrial and biological fluids, are well known. Despite the wide variety of tests which have been developed for the determination of specific constituents in fluids, a similarity exists in the steps associated with each process. For example, a suitable sample or specimen must be acquired, which in the case of body fluids means that a suitable urine, blood, etc. specimen must be obtained from a patient. The specimen or sample must then be suitably stored and preserved if not analyzed immediately. Frequently, the specimen must be prepared by centrifugation, filtration, dilution, etc. and then reacted with appropriate chemical reagents. Ultimately, it is necessary to abstract information about the specimen or sample by transducing a chemical signal, which can be a color change, into an electronic signal which in turn can be processed and combined with other relevant data to arrive at a final assessment of a specific constituent present in the sample or specimen, thereby facilitating a clinical decision.

Conventional liquid reagent systems tend to be complicated, time consuming and expensive. In the case of optical systems a light source has to be provided, a spectral or intensity change has to occur during reagent-sample interaction, and this change must be detected and processed.

The essential steps needed for electrochemical analysis systems are reduced somewhat, but still require an amperometric probe device having a constant voltage source, a specific electrode and a current monitor.

Reagent strip test devices have enjoyed wide use in many analytical applications, especially in the chemical analysis of biological fluids, because of their relatively low cost, ease of usability and speed in obtaining results. In medicine, for example, numerous physiological functions can be monitored merely by dipping reagent strip test devices into a sample of body fluid, such as urine or blood, and observing a detectable response such as a change of color or a change in the amount of light reflected from or adsorbed by the reagent strip test device. An optical device, such as a reflectance photometer, is required in order to automate or semiautomate the analysis of reagent strip test devices.

Ideally, an analytical device and method for detecting a constituent in a sample should comprise a nonoptical sensing element which has no electrodes, requires no direct current connection, requires no membrane, is inexpensive to the point of being disposable, is specific and sensitive, is rapid in response, is easy to use and can be employed directly with an unmodified specimen.

Techniques for making quantitative chemical determinations and estimations through measurement of the change in conductivity of a test system before and after reaction of the substance to be detected with a test reagent are generally known. For example, one method for the quantitative determination of an enzyme or substrate involves the measurement of the change in electrical conductivity of the test system resulting from interaction of the enzymes and substrate. This is described in an article entitled "Conductivity Method for Determination of Urea" by W. T. Chin et al. published in *Analytical Chemistry,* Nov. 1961, at pages 1757–1760. This method measures the electrical conductivity in a test fluid containing urea before and after reaction with urease and thereafter requires calculations to be made of the change in conductivity.

Another method for analytically studying the elements of an enzyme-substrate reaction is disclosed in U.S. Pat. No. 3,421,982. The apparatus disclosed in U.S. Pat. No. 3,421,982 includes circuitry which requires continuous manual adjustment to obtain a measurement of the change in conductivity upon reaction of test fluid and reagent. Moreover, the method is based on the assumption that the reaction produces a linear rate of change of conductivity.

U.S. Pat. No. 3,635,681 provides differential conductivity measuring apparatus comprising a pair of probes, each of which includes a pair of spaced electrodes. Electrodes of the first probe are in intimate contact with a test reagent, such as an enzyme, incorporated within the matrix. The electrodes of the second probe are also in intimate contact with a matrix. In use, the first and second probes are contacted with an ionic medium containing the substance to be detected. The conductivity measured by the second probe is dependent upon the conductivity of the matrix means associated with the electrodes of said probe and the ionic medium and the conductivity of the first probe is dependent upon the conductivity of the ionic medium and the matrix means associated with the electrodes of the first probe, as well as upon any change in conductivity produced by a chemical reaction.

A. J. Frank and Kenji Honda, "Polypyrrole Coated Semiconductor Electrodes", *J. Electrochem. Soc.,* 82–1:992 (1982), disclose the use of a transition metal catalyst (Ru) painted onto polymer to protect CdS and CdSe semiconductor electrodes from photocorrosion in aqueous electrolyte.

N. N. Savvin, E. E. Gutman, I. A. Myasnikov and V. P. Bazov, *Kinet. Catal.,* 19(3):634–636 (1978), "Investigation of the Elementary Stages of the Catalytic Decomposition of Hydrogen Peroxide on Metal Oxides by Conductometric Analysis and IR Spectroscopy" have shown, on the basis of experimental data, that the primary event in the decomposition of hydrogen peroxide on metal oxides (ZnO and NiO) involves preferential rupture of the O—O bond in the $H_2O_2$ molecule to form chemisorbed hydroxyl radicals. The superstoichiometric metal atoms in the oxides can act as active centers for the decomposition of hydrogen peroxide in the gas phase. Conductivity changes are observed in the catalyst (ZnO, NiO).

The reaction of $FeCl_3$ dissolved in dry nitromethane with polyacetylene, $(CH)_x$, results in the formation of p-type conducting polymers ($O=780$ ohm$^{-1}$) according to A. Pron, D. Billaud, I. Kulszewicz, C. Budrowski, J. Przyluski, and J. Suwalski, "Synthesis and Characterization of New Organic Metals Formed by Interaction of $FeCl_3$ with Polyacetylene $(CH)_x$ and Poly(-para)phenylene $(C_6H_6)_x$", *Mat. Res. Bull.,* 16: 1229–1235 (1981). IR spectra of $(CH_x)$ lightly doped with $FeCl_3$ exhibit the formation of two new bands characteristic of other p-type dopants of $(CH)_x$. Mössbauer spectroscopy shows that the anion formed in the reaction is a high spin $Fe^{II}$ complex. The doping causes significant change in $(CH)_x$ interchain distances as evidenced by X-ray diffraction. Similar reaction occurs between poly(para)phenylene, $(C_6H_4)_x$ and $FeCl_3$ causing the increase of the conductivity of compressed poly(para)phenylene powder to metallic regime. The reaction mechanism is more complex than in the case of $(CH)_x$ since Mössbauer spectroscopy shows the existence of two types of $Fe^{II}$ iron ions.

A quantitative theory of the electrode surface conductance decrease caused by absorbed ions is discussed by W. J. Anderson and W. N. Hansen, "Electrode Surface Conductance Measurements in an Electrochemical Cell", *J. Electrochem. Soc.*, 121(12):1570–1575 (1974). Conductance measurements are shown to provide a reliable measure of absorbed ion surface concentration. Changes in the absorbed state are detected as a function of electrode potential. The conductance measurements are used to measure the ionic diffusion rate of $I^-$ through an aqueous electrolyte.

U.S. Pat. No. 4,334,880 describes a polyacetylene element in which the electrical characteristics of a specific binding substance, such as an antibody molecule, is used to influence the conductivity state of the polyacetylene element.

R. A. Bull, F. R. Ran, A. J. Bard, "Incorporation of Catalysts into Electronically Conductive Polymers: Iron Phthalocyanine in Polypyrrole", *J. Electrochem. Soc.*, 130(7):1636 (1983) disclose the deposition of polymer onto a glassy carbon electrode and current voltage properties are studied in a traditional electrochemical system with opposing electrodes. No conductivity changes in the polymer are mentioned.

W. W. Harvey, "Conductance of Germanium in Contact with Aqueous Electrolytes", *Am. N.Y. Acad. Sci.*, 101:904–914 (1963), teaches the passage of current parallel to the interface in a semiconductor contacting an electrolyte to obtain electrolytic polarization of the interphase. A portion of the longitudinal current flows in the electrolyte. Since a substantial fraction of an applied semiconductor-electrolyte potential difference falls within the space charge region of the semiconductor, the semiconductor surface potential varies with position as a consequence of the polarization attending longitudinal current flow.

U.S. Pat. No. 3,574,072 describes the electrochemical polymerization of hetrocyclic compounds, including pyrrole.

SUMMARY OF THE INVENTION

An object of the present invention is to provide polymer-catalyst transducers for detecting a constituent in a sample.

Another object of the present invention is to provide polymer-catalyst transducers capable of being used with an unmodified specimen, e.g., whole blood, as an analyte.

Yet another object of the invention is to provide a nonoptical, low cost, electrical contact or noncontact method of determining a constituent in a sample.

Still another object of the invention is to provide polymer-catalyst transducers which are small in size and disposable in format.

In accordance with the present invention, polymer-catalyst transducers are prepared by incorporating metal organic or metal inorganic catalyst into a polymer of a nuclearly unsaturated heterocyclic compound to obtain a material which changes conductivity during the catalytic decomposition of hydrogen peroxide. Changes in conductivity in the resulting transducers, as the result of electron density changes, are measured to provide an indication of a particular constituent present in the sample. In one embodiment, a conductivity meter is coupled to a polymer-catalyst transducer to measure conductivity changes during reaction with the analyte sample to be measured. The resulting polymer-catalyst transducers are especially useful in determining the presence of glucose in whole blood.

DESCRIPTION OF THE PREFERRED EMBODIMENTS

Figure 1:
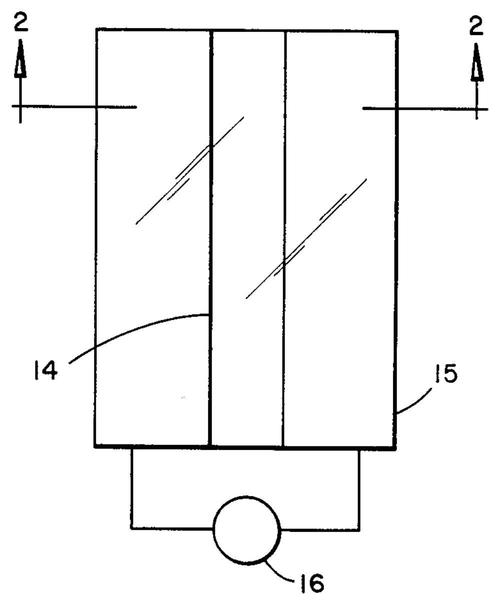
FIG. 1 is a schematic top view of apparatus described in Example VI.
Figure 2:
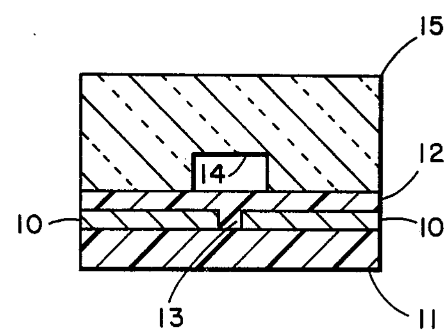
FIG. 2 is a schematic cross-sectional view of the apparatus in FIG. 1 taken along lines 2—2.
Figure 3:
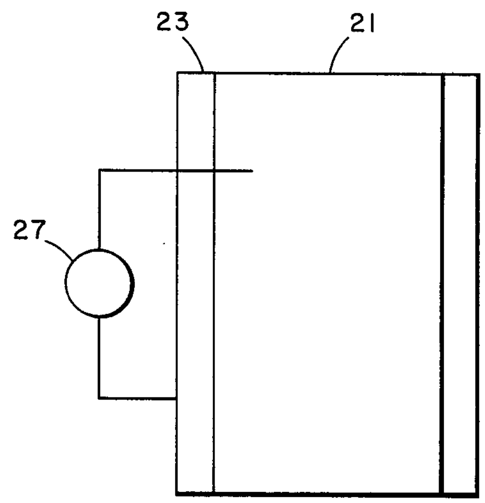
FIG. 3 is a schematic top view of apparatus in accordance with Example VII.
Figure 4:
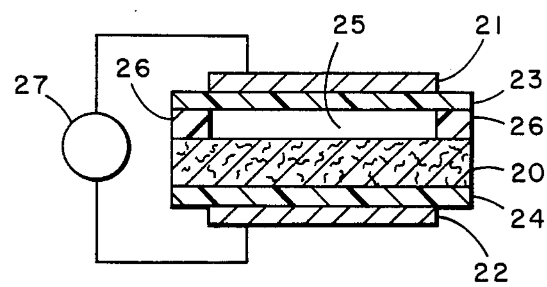
FIG. 4 is a schematic cross-sectional front view of the apparatus in FIG. 3.

The polymer-catalyst transducers of the present invention can be envisioned as comprising polymer with catalytic sites for hydrogen peroxide decomposition contained therein.

The polymer utilized in the present invention is a nuclearly unsaturated heterocyclic compound selected according to criteria which includes the ability to control parameters of the polymer, the stability of the polymer, the availability of starting material, the ability to derivatize the polymer, the ability to effect conductivity adjustments, the morphology of polymer and the absence of interferences with fluids to be tested or analyzed. Pyrrole, thiophene, pyridine, furan, and purine polymers, both homopolymers and copolymers, were selected in accordance with this criteria. Included as monomers, for example, one can use 5- or 6-membered ring compounds which may, if desired, contain substituents. These substituents can be selected from the group consisting of halogen, aromatic, alkyl, of from 1 to 20 carbon atoms, cycloalkyl, alkaryl, aralkyl, alkoxy, acyl, etc., radicals, 2-methylfuran, 3-methylfuran, 2-ethylfuran, 3-ethylfuran, 3-n-butylfuran, 2-n-pentylfuran, 3-decylfuran, 2-tetradecylfuran, 2,3-dimethylfuran, 2,3-diethylfuran, 3,4-di-n-propylfuran, 3,4-didodecylfuran, 2-chlorofuran, 3-bromofuran, 3,4-dichlorofuran, 2,3-diiodofuran, 3,4-difurylfuran, 2-phenylfuran, 3-benzylfuran, 2-(p-tolyl)furan, 2-cyclopentylfuran, 3-cyclohexylfuran, 3-methoxyfuran, 2-ethoxyfuran, 3,4-dipropoxyfuran, 2-acetylfuran; 2-methylthiophene, 3-methylthiophene, 2-ethylthiophene; 3-ethylthiophene, 3-n-butylthiophene, 2-tetradecylthiophene, 2,3-dimethylthiophene, 2,3-diethylthiophene, 3,4-di-n-propylthiophene, 3,4-didodecylthiophene, 2-chlorothiophene, 3-bromothiophene, 3,4-dichlorothiophene, 2,3-diiodothiophene, 3,4-difurylthiophene, 2-phenylthiophene, 3-benzylthiophene, 2-(p-tolyl)thiophene, 2-cyclopentylthiophene, 3-cyclohexylthiophene, 3-methoxythiophene, 2-ethoxythiophene, 3,4-dipropoxythiophene, 2-acetylthiophene; 2-methylpyrrole, 3-methylpyrrole, 2-ethylpyrrole, 3-ethylpyrrole, 3-n-butylpyrrole, 2-n-pentylpyrrole, 3-decylpyrrole, 2-tetradecylpyrrole, 2,3-dimethylpyrrole, 2,3-diethylpyrrole, 3,4-di-n-propylpyrrole, 3,4-didodecylpyrrole, 2-chloropyrrole, 3-bromopyrrole, 3,4-dichloropyrrole, 2,3-diiodopyrrole, 3,4-difurylpyrrole, 2-phenylpyrrole, 3-benzylpyrrole, 2-(p-tolyl)pyrrole, 2-cyclopentylpyrrole, 3-cyclohexylpyrrole, 3- methoxypyrrole, 2-ethoxypyrrole, 3,4-dipropoxypyrrole, 2-acetylpyrrole; 2-methylpyran, 3-methylpyran, 2-ethylpyran, 3-ethylpyran, 3-n-butylpyran, 2-n-pentylpyran, 3-decylpyran, 2-tetradecylpyran, 2,3-dimethylpyran, 2,3-diethylpyran, 3,4-di-n-propylpyran, 3,4-didodecylpyran, 2-chloropyran, 3-bromopyran, 3,4-dichloropyran, 2,3-diiodopyran, 3,4-difurylpyran, 2-phenylpyran, 3-benzylpyran, 2-(p-tolyl)pyran, 2-cyclopentylpyran, 3-cyclohexylpyran, 3-methoxypyran, 2-ethoxypyran, 3,4-dipropoxypyran, 2-acetylpyran; 2-methylthiapyran, 3-methylthiapyran, 2-ethylthiapyran, 3-ethylthiapyran, 3-n-butylthiapyran, 2-n-pentylthiapyran, 3-decylthiapyran, 2-tetradecylthiapyran, 2,3-dimethylthiapyran, 2,3-diethylthiapyran, 3,4-di-n-propylthiapyran, 3,4-didodecylthiapyran, 2-chlorothiapyran, 3-bromothiapyran, 3,4-dichlorothiapyran, 2,3-diiodothiapyran, 3,4-difurylthiapyran, 2-phenylthiapyran, 3-benzylthiapyran, 2-(p-tolyl)thiapyran, 2-cyclopentylthiapyran, 3-cyclohexylthiapyran, 3-methoxythiapyran, 2-ethoxythiapyran, 3,4-dipropoxythiapyran, 2-acetylthiapyran; 2-methylpyridine, 3-methylpyridine, 2-ethylpyridine, 3-ethylpyridine, 3-n-butylpyridine, 2-n-pentylpyridine, 3-decylpyridine, 2-tetradecylpyridine, 2,3-dimethylpyridine, 2,3-diethylpyridine, 3,4-di-n-propylpyridine, 3,4-didodecylpyridine, 2-chloropyridine, 3-bromopyridine, 3,4-dichloropyridine, 2,3-diiodopyridine, 3,4-difurylpyridine, 2-phenylpyridine, 3-benzylpyridine, 2-(p-tolyl)pyridine, 2-cyclopentylpyridine, 3-cyclohexylpyridine, 3-methoxypyridine, 2-ethoxypyridine, 3,4-dipropoxypyridine, 2-acetylpyridine; etc. Advantageously, the resulting polymer can be derivatized to contain carboxyl or amino groups for immobilization of enzymes.

In contrast, other materials, even polymers which have been utilized in semiconducting applications, such as polyacetylene, polycarotene, etc., were found to satisfy only four or less of the seven criteria listed above.

The polymeric material can be synthesized by an electrochemical method disclosed by Diaz, "Electrochemical Preparation and Characterization of Conducting Polymers", *Chemica Scripta,* 17:145–148 (1981). For example, pyrrole in acetonitrile, with tetraethylammonium tetrafluoroborate as an electrolyte, can be electropolymerized on a precious metal anode in an undivided electrochemical cell under conditions which exclude oxygen, e.g., an inert gas. The polymer forms a dense, microscopically globular, insoluble and stable film on the anode. The thickness can be controlled by monitoring the total charge passed through the circuit. Polypyrrole chains thus formed incorporate anions from the electrolyte, typically in the ratio of 4 pyrrole units to 1 anion.

Although iron is a preferred material (anion) for the central metal atom of the catalyst, other Group VIII members of the periodic table can be employed including cobalt, nickel, ruthenium, rhodium, platinum, osmium, iridium and palladium. In general, transition metal complex anions and metal complex anions, derivatized to be in anionic form, can be employed. Ultimately, the choice depends on the relative cost of the metal and its availability. Other anions can be substituted, e.g., hexacyanoferrate or Cu-tetrasulfophthalocyanine. In any event, the total conductivity of the resulting polymer-catalyst transducers ranges between $10^{-3}$ $Scm^{-1}$ to 100 $Scm^{-1}$.

Among metal organic catalysts which can be employed are the metalphthalocyanines and metalporphyrins. The phthalocyanines (Pc) can be derivatized with ionic groups to make them more soluble in organic electrolytes and desired ionic characteristics can also be produced by photoexcitation. Examples of preferred metal-phthalocyanines include iron tetrasulfonated phthalocyanine, cobalt tetrasulfonated phthalocyanine and ruthenium tetrasulfonated phthalocyanine.

The catalytic properties of metal porphyrins have also been investigated extensively, mostly in conjunction with studies of catalase and peroxidase enzymes. M. M. Taque Khan et al. "Homogeneous Catalysis by Metal Complexes", Vol. 1, p. 139, *Acad. Press,* New York (1974). Ionic forms are commercially available from Strem Chemicals, Inc., Newburyport, Md. Preferred metal porphyrins (P) include iron, ruthenium and cobalt tetrasulfonated prophyrins.

Thus, by using metal organic or metal inorganic material, suitably ionized by derivatization or photoenergetically by illumination using a xenon light source, as the anion and electrolyte, e.g., dimethyl formamide, acetonitrile, methylene chloride, etc., together with nuclearly unsaturated heterocyclic compound a catalytically active molecule can be formed into a semiconducting organic polymer-catalyst transducer.

Since the polymer is formed by the process of electropolymerization, suitable substrate material must be involved. The precise nature of the substrate material is not critical. Suitable conductive substrate materials include platinum, gold, rhodium, titanium, tantalum, nickel, stainless steel No. 314, etc. Suitable semiconductor substrate materials include materials such as silicon, germanium, GaAs, etc. Transparent substrate materials can also be used, including tin oxide and indium titanium oxide. In addition, glassy carbon can be used. Each of these materials offers certain advantages; platinum has well known properties as an electrode material, but polymer tends to adhere to the surface and must be lifted off. After the film is lifted, the contact surface then becomes the active surface for conductivity measurements in the presence of analyte. Titanium is an attractive choice because the metal can be changed to the oxide by exposure to oxygen at an elevated temperature and the resulting titanium oxide is an insulator.

Polyacetylene, when doped with oxygen increases its conductivity to the extent that it can also serve as a suitable substrate. It exhibits a fibrillar structure which increases the surface area of deposited polymer film. Following electropolymerization, the polyacetylene can be converted to an insulator by further exposure to oxygen according to known procedures such as set forth by J. M. Pochan et al. in "Kinetics of Doping and Degradation of Polyacetylene by Oxygen", *Macromolecules,* 14:110–114 (1981).

After the polymerized film is removed from the substrate material, electrodes can be attached directly, e.g., by plating, onto the film for DC measurements or a conductor-insulator film sandwich can be formed for AC conductivity measurements in the presence of an analyte. Glucose oxidase, enzymatically converts glucose to gluconic acid and hydrogen peroxide. Likewise, other enzymes follow a similar mechanism. For example, uricase enzymatically converts uric acid to allantoin and hydrogen peroxide.

Examples I–V demonstrate the preparation of various polymer-catalyst materials capable of reflecting electron density changes by changes of conductivity. Polypyrrole tetrachloroferrate, polypyrrole iron tetrasulfophthalocyanine and other related materials were synthesized electrochemically by direct deposition onto metal (e.g., platinum, rhodium, titanium, etc.) electrodes. The pyrrole-catalyst materials, although stable in air, were stored in sealed polyester/polyolefin pouches.

EXAMPLE I—SYNTHESIS OF POLYPYRROLE TETRACHLOROFERRATE

The preparation of polypyrrole tetrachloroferrate was accomplished by reacting tetraethylammoniumtetrachloroferrate (III) and pyrrole. The pyrrole was obtained from Eastman Kodak and purified by distilling the material over calcium hydride under an argon atmosphere. Polymerization was accomplished following the procedure described by A. F. Diaz and K. K. Kanazawa, "Polypyrrole: An Electrochemical Approach to Conducting Polymers" in "Extended Linear Chain Compounds". Vol. 3 Ed. J. S. Miller Plenum Press, N.Y. 1983.

The tetraethylammoniumtetrachloroferrate (III) was obtained by dissolving 6.825 grams (g) of ferric chloride, obtained from Mallinckrodt, in 40 milliliters (ml) of ethyl alcohol. 4.145 g of tetraethylammonium chloride, obtained from Aldrich, was dissolved in 10 ml of ethanol. The two solutions were then mixed resulting in a yellow precipitate. The precipitate was filtered and washed with ethanol. Recrystallization from acetonitrile-ethanol yielded yellow needles which were washed with ethanol and air dried.

The resulting tetraethylammoniumtetrachloroferrate (III) [0.1 molar (M)] was then reacted with 0.1M of pyrrole in the presence of 50 ml of acetonitrile under an argon atmosphere employing a three electrode cell having working/counter platinum electrodes located about 1.5 centimeters (cm) apart and a Ag/Ag $N0_3$ (acetonitrile) reference electrode. The potential was controlled at +0.5 volts (V) relative to the reference electrode using a Princeton Applied Research (PAR) Model 363 potentiostat. After 2½ hours the reaction was stopped and the resulting film (having a thickness less than 0.3 mil) was washed with acetonitrile before using a piece of Scotch brand adhesive tape to remove the film from the electrode. The resulting black film was flexible, did not have any pinholes or other structural imperfections and had a conductivity of greater than 10 S/cm (Siemens per centimeter), as measured using a Model 1000 AR Lehighton Electronics Inc. (Lehighton, Pa.) conductivity meter, operating at 10 megahertz (MHz) in a contactless mode.

It has also been found that following a similar procedure polypyrrole tetrachloroferrate can be prepared in the presence of a matrix material, such as filter paper, to enhance the strength and flexibility of the resulting polymer-catalyst transducer.

EXAMPLE II—SYNTHESIS OF POLYPYRROLE IRON TETRASULFOPHTHALOCYANINE

The synthesis of Example I was followed using pyrrole, from Eastman Kodak, purified by distilling over calcium hydride under an argon atmosphere before use, and tetraethylammonium iron tetrasulfophthalocyanide as the anion. The sodium salt of iron tetrasulfophthalocyanide was prepared employing the procedure described by Weber and Busch, *Inorg. Chem.*, 4:469 (1965), using ferrous sulfate from Fisher, 4-sulfophthalic acid from Kodak, sodium bicarbonate from Mallinckrodt, ammonium molydate from Fisher, urea from Mallinckrodt, nitrobenzene from Aldrich and tetraethylammonium hydroxide from Aldrich. The conversion of the sodium salt to the tetraethylammonium salt was accomplished using ion-exchange columns.

The resulting black film (polypyrrole iron tetrasulfophthalocyanine) formed on the platinum electrode had a conductivity of 1 S/cm.

EXAMPLE III—SYNTHESIS OF POLYPYRROLE TETRACHLORORUTHENATE

Tetraethylammonium tetrachlororuthenate was prepared by reacting one gram of ruthenium (III) chloride from Alfa dissolved in approximately 90 ml of ethanol with 0.8 g of tetraethylammonium chloride from Aldrich dissolved in ethanol. The resulting red-brown precipitate was filtered, washed with ethanol and then recrystallized from an acetonitrile-ethanol solution to yield red-brown microcrystals.

Polypyrrole tetrachlororuthenate was prepared following the procedure of Example I using 0.01M acetonitrile solution of tetraethylammonium tetrachlororuthenate at a potential of +0.7 V, instead of 0.5 V, for a reaction time of three hours. The resulting black film had a thickness of 5 mils and a conductivity of approximately 0.3 S/cm, measured as in Example I.

EXAMPLE IV—SYNTHESIS OF POLYPYRROLE TETRA(4-SULFOPHENYL)-MESO-IRON PORPHYRIN

Following the procedure of Fleischer et al., *J. of Amer. Chem. Soc.*, 93:3162 (1971), metal ion was incorporated into porphyrin. Specifically, 0.9 g of tetrasodium-meso-tetra(4-sulfonatophenyl) porphyrin (12 hydrate) from Porphyrin Products in 50 ml of distilled water was added to ferrous sulfate from Fisher. The resulting mixture was heated at approximately 120° C. and stirred. The pH was adjusted to approximately 7.5 by adding sodium carbonate and heating the mixture 35 minutes using the steam bath. The pH was then adjusted to 3 by adding 50 percent solution of sulfuric acid. The conversion of the sodium salt to the tetraethylammonium salt was accomplished using ion exchange columns.

Following the procedure of Example I, using 0.002 M of anion and 0.1M of pyrrole with a potential of +0.7 V for a reaction of time of 18 hours, a film of polypyrrole tetra(4-sulfophenyl)-meso-iron porphyrin was obtained having conductivity of approximately 1 S/cm.

EXAMPLE V—SYNTHESIS OF POLYTHIOPHENE TETRACHLOROFERRATE

The preparation of polythiophene tetrachloroferrate was accomplished by treating tetraethylammonium tetrachloroferrate (III) and bithiophene. The bithiophene was obtained from Aldrich chemical as crystalline solid and was used without further purification. Polymerization was accomplished following the procedure described by Mark A. Druy and Robert J. Seymour (American Chemical Society Meeting Abstract, 1983, Seattle).

Polythiophene tetrachloroferrate was prepared following the procedure of Example I using an acetonitrile solution of 0.004M bithiophene and 0.05M tetraethylammonium tetrachloroferrate (III) at a potential of +0.9 V instead of 0.5 V for a reaction time of two hours.

A black film was obtained having conductivity of approximately 0.1 S/cm.

In addition to polymerization in the presence of filter paper (as mentioned in Example I) it is also possible to effect polymerization in the presence of silicon rubber tubing. By swelling the tubing in methylene chloride polymer and catalyst penetrate the tubing and polymerization occurs inside the tubing.

EXAMPLE VI

Polypyrrole tetrachlororuthenate was prepared as in Example III except that it was deposited onto a gold electrode 10 (750Å thick) supported by Kapton (0.5 mil thick). The electrode was 1.25 inches (in.) long and, 0.5 in. wide with a cut lengthwise down the middle. The polymer 12 deposited onto the gold, filling the gap 13 between the two halves. This resulting structure was then washed in acetonitrile and clamped to a flow channel 14 (0.8 in.×0.1 in.) milled into a Lucite block 15. An aqueous solution of peroxidase enzyme in 0.05M phosphate buffer, pH 7.0 in a concentration of 10 mg/ml was then recirculated through the flow channel using a peristaltic pump at a flow rate of 0.1 ml/min. for 4 hrs., followed by a solution of 0.25 percent glutaraldehyde, also recirculated for 14 hrs. The absorbed protein was then washed in 0.85 percent NaCl solution, followed by distilled $H_2O$ and exposed to a solution of glucose oxidase enzyme in 0.05M phosphate buffer for 4 hrs., again recirculating through the flow channel. This second enzyme was again crosslinked with 0.25 percent glutaraldehyde solution as before, washed in 0.85 percent NaCl and distilled $H_2O$.

The polymer with absorbed and crosslinked peroxidase and glucose oxidase was then exposed to various concentrations of glucose, starting with 25 mg/dl (milligrams per deciliter). The conductivity of the polymer was monitored at 20 KHz (kilohertz) on an Hewlett Packard Model 4192A Impedance Analyzer 16. A DC bias voltage was also applied on the sample sweeping from −5 VDC to +5 VDC. A peak appeared in the otherwise parabolic response curve which changed with glucose concentration.

EXAMPLE VII

This example demonstrates AC contactless impedance measurement of polymer prepared as in Example I in the presence of filter paper 20, which was cut into a strip and sandwiched into a flow cell consisting of electrodes of copper foil 21 and 22 on Kapton 23 and 24. The insulator (0.5 mil thick) was facing the flow channel 25 containing the strip of filter paper-polymer material. A small fluid gap was maintained around the filter paper with silicone spacers 26 which also confined the fluid in the flow channel.

A similar arrangement of contactless impedance measurement can also be performed with a interdigited electrode system instead of a sandwich. In this case only one side of the capacitor configuration is necessary. The copper foil is photolithographically defined into a interdigited pattern supported on Kapton (polyimide), which contacts the filter paper impregnated with polymer material. The fluid channel is provided by silicone and a glass slide is clamped to the electrode.

Similar results were obtained by both arrangements. The impedance change measured by analyzer 27 at 100 KHz was linearly proportional to $H_2O_2$ concentration.

From the foregoing, it will be seen that this invention is well adapted to attain all of the ends and objects hereinabove set forth, together with other advantages which are obvious and which are inherent to the system. The invention has the advantages of convenience, simplicity, relative inexpensiveness, positiveness, effectiveness, durability, accuracy and directness of action. Among the advantages of the proposed polymer-catalyst transducers are the fact that the transducers operate nonoptically, can be constructed at relatively low cost, have a great degree of flexibility with respect to format, can operate on a noncontact basis which overcomes problems usually encountered with electrochemical techniques and can be constructed to have a relatively small size. The invention substantially eliminates problems associated with pretreatment of samples.

It should be understood that many possible configurations of the polymer-catalyst transducers exist. The polymer-catalyst transducers can be in the form of fine powder, in the form of a film or in the form of a gel. If not self supporting, the polymer-catalyst transducers are suitably attached to a substrate. For purposes of exterior support, the polymer-catalyst film can be applied to suitable substrate by known coating or adhesion methods. By arranging multiple polymer-catalyst transducers in parallel, it is possible to simultaneously analyze an analyte for different constituents.

While the present invention is primarily directed to polymer-catalyst transducer for detecting various clinically significant substances or constituents in biological fluids, such as urine and blood, including lysed or unlysed blood, blood plasma, blood serum, etc., it should be understood that the transducers can be utilized for the detection of nonbiological fluids, including swimming pool water, wines, etc. The polymer catalyst transducers can also be used to detect combustion products, e.g., determining contents of smoke stacks, etc.

Obviously, many other modifications and variations of the invention as hereinbefore set forth can be made without departing from the spirit and scope thereof.

What is claimed is:

1. Apparatus for detecting a constituent in a fluid sample by measuring changes in conductivity, said apparatus comprising:

- a polymer catalyst transducer consisting essentially of a metal-organic or metal-inorganic catalyst and a polymer of a nuclearly unsaturated heterocyclic compound;
- metal electrodes in either direct or indirect contact with the polymer catalyst transducer for detecting changes in the conductivity of said polymer catalyst transducer when said transducer is contacted with a fluid sample; and
- means connected to said electrodes for measuring changes in the conductivity of the polymer catalyst transducer.

2. The apparatus of claim 1 which also includes a flow chamber, in which said polymer catalyst transducer is positioned, which brings a fluid sample into contact with said polymer catalyst transducer inside said flow chamber.

3. The apparatus of claim 1 in which the electrodes are constructed of a metal selected from the group consisting of gold, platinum, rhodium or titanium.

4. The apparatus of claim 1 in which the catalyst is an organic or inorganic metal compound wherein the metal is a Group VIII member of the periodic table.

5. The apparatus of claim 1 in which the catalyst is metal phthalocyanine.

6. The apparatus of claim 1 in which the catalyst is a metal porphyrin.

7. The apparatus of claim 1 in which the polymer catalyst transducer comprises polypyrrole tetrachloroferrate.

8. The apparatus of claim 1 in which the polymer catalyst transducer comprises polypyrrole iron tetrasulfophthalocyanine.

9. The apparatus of claim 1 in which the polymer catalyst transducer comprises polypyrrole tetracholororuthenate.

10. The apparatus of claim 1 in which the polymer catalyst transducer comprises polythiophene tetrachloroferrate.

* * * * *